(12) United States Patent
Nappa et al.

(10) Patent No.: US 9,102,580 B2
(45) Date of Patent: Aug. 11, 2015

(54) CATALYTIC FLUORINATION PROCESS OF MAKING HYDROHALOALKANE

(71) Applicants: Mario Joseph Nappa, Newark, DE (US); Andrew Jackson, Newark, DE (US); Daniel C. Merkel, West Seneca, NY (US)

(72) Inventors: Mario Joseph Nappa, Newark, DE (US); Andrew Jackson, Newark, DE (US); Daniel C. Merkel, West Seneca, NY (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 14/357,345

(22) PCT Filed: Nov. 9, 2012

(86) PCT No.: PCT/US2012/064322
§ 371 (c)(1),
(2) Date: May 9, 2014

(87) PCT Pub. No.: WO2013/071024
PCT Pub. Date: May 16, 2013

(65) Prior Publication Data
US 2014/0309462 A1    Oct. 16, 2014

Related U.S. Application Data

(60) Provisional application No. 61/558,081, filed on Nov. 10, 2011, provisional application No. 61/558,086, filed on Nov. 10, 2011.

(51) Int. Cl.
| | | |
|---|---|---|
| C07C 17/087 | (2006.01) | |
| C07C 17/25 | (2006.01) | |
| C07C 17/38 | (2006.01) | |
| C07C 17/20 | (2006.01) | |
| B01J 37/26 | (2006.01) | |
| B01J 27/12 | (2006.01) | |
| B01J 27/135 | (2006.01) | |

(52) U.S. Cl.
CPC ............. *C07C 17/38* (2013.01); *B01J 27/12* (2013.01); *B01J 27/135* (2013.01); *B01J 37/26* (2013.01); *C07C 17/087* (2013.01); *C07C 17/206* (2013.01); *C07C 17/25* (2013.01)

(58) Field of Classification Search
CPC .... C07C 17/38; C07C 17/206; C07C 17/087; C07C 17/25; B01J 27/135; B01J 27/12; B01J 37/26

USPC .................................. 570/155, 168, 177
See application file for complete search history.

(56) References Cited

U.S. PATENT DOCUMENTS

| | | |
|---|---|---|
| 2,439,299 A | 4/1948 | Hovey et al. |
| 3,258,500 A | 6/1966 | Swamer |
| 3,823,195 A | 7/1974 | Smith |
| 4,967,024 A | 10/1990 | Gumprecht et al. |
| 5,202,509 A | 4/1993 | Laviron et al. |
| 5,227,546 A | 7/1993 | Eicher et al. |
| 5,283,381 A | 2/1994 | Eicher et al. |
| 5,336,817 A | 8/1994 | Eicher et al. |
| 5,620,936 A | 4/1997 | Felix et al. |
| 5,728,639 A | 3/1998 | Felix |
| 6,011,185 A | 1/2000 | Yoshimura et al. |
| 6,049,016 A | 4/2000 | Yoshimura et al. |
| 7,786,334 B2 | 8/2010 | Belter |
| 8,058,486 B2 | 11/2011 | Merkel et al. |
| 2009/0018376 A1 | 1/2009 | Belter |
| 2009/0018377 A1 | 1/2009 | Boyce |
| 2009/0182179 A1 | 7/2009 | Merkel et al. |
| 2009/0240090 A1 | 9/2009 | Merkel et al. |
| 2010/0036179 A1 | 2/2010 | Merkel et al. |
| 2010/0105967 A1 | 4/2010 | Nappa |
| 2010/0137658 A1 | 6/2010 | Merkel et al. |
| 2011/0105807 A1 | 5/2011 | Kopkalli et al. |
| 2011/0144216 A1 | 6/2011 | Hulse et al. |
| 2012/0097885 A9 | 4/2012 | Hulse et al. |

FOREIGN PATENT DOCUMENTS

| | | |
|---|---|---|
| CN | 101597209 A | 12/2009 |
| CN | 101665403 A | 3/2010 |
| WO | 2009/137658 A2 | 11/2009 |
| WO | WO 2011/087825 A1 | 7/2011 |

OTHER PUBLICATIONS

International Search Report dated Mar. 22, 2013 issued in PCT/US2012/064322.
Chinese Office Action and Chinese Search Report dated Mar. 23, 2015 issued in Application No. 201280066728.3 (in English and in Chinese).

*Primary Examiner* — Shailendra Kumar
(74) *Attorney, Agent, or Firm* — Scully, Scott, Murphy & Presser, P.C.

(57) ABSTRACT

The present disclosure provides a fluorination process which involves reacting a hydrohaloalkene of the formula $R_fC$—$Cl$=$CH_2$ with HF in a reaction zone in the presence of a fluorination catalyst selected from the group consisting of $TaF_5$ and $TiF_4$ to produce a product mixture containing a hydrohaloalkane of the formula $R_fCFClCH_3$, wherein $R_f$ is a perfluorinated alkyl group.

22 Claims, No Drawings

CATALYTIC FLUORINATION PROCESS OF MAKING HYDROHALOALKANE

CROSS REFERENCE TO RELATED APPLICATIONS

This application is a '371 of PCT Application No. PCT/US2012/064322, which was filed on Nov. 9, 2012 and claims priority of U.S. provisional applications U.S. Ser. No. 61/558,081 and 61/558,086, both of which were filed on Nov. 10, 2011; the contents of both of these provisional applications are incorporated by reference.

BACKGROUND

1. Field of the Disclosure

This disclosure relates in general to catalytic fluorination processes of making hydrohaloalkanes. More particularly, this disclosure relates to fluorination reactions of hydrohaloalkenes with HF using $TaF_5$ or $TiF_4$ as catalysts.

2. Description of Related Art

Hydrohaloalkanes, such as HCFCs (hydrochlorofluorocarbons), can be employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. They are also useful as intermediates to HFOs (hydrofluoroolefins) which not only are safe for the stratospheric ozone layer but also have low global warming potentials (GWPs).

BRIEF SUMMARY OF THE DISCLOSURE

The present disclosure provides a fluorination process which comprises reacting a hydrohaloalkene of the formula $R_fCCl=CH_2$ with HF in a reaction zone in the presence of a fluorination catalyst selected from the group consisting of $TaF_5$ and $TiF_4$ in an amount effective and under conditions to produce a product mixture comprising a hydrohaloalkane of the formula $R_fCFClCH_3$, wherein $R_f$ is a perfluorinated alkyl group without substantially forming $R_fCF_2CH_3$. These reactions are conducted under conditions which promote the formation of $R_fCFClCH_3$ and minimize the production of $R_fCF_2CH_3$ and $R_fCHClCH_2F$.

DETAILED DESCRIPTION

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

The term "dehydrochlorinating", "dehydrochlorination" or "dehydrochlorinated", as used herein, means a process during which hydrogen and chlorine on adjacent carbons in a molecule are removed.

The term "alkyl", as used herein, either alone or in compound words such as "perfluorinated alkyl group", includes cyclic or acyclic and straight-chain or branched alkyl groups, such as, methyl, ethyl, n-propyl, i-propyl, or the different isomers thereof. It includes, for example, straight or branched chain alkyl groups containing from 1 to 6 carbon atoms and cyclic alkyl groups containing 3 to 6 ring carbon atoms and up to a total of 10 carbon atoms.

The term "perfluorinated alkyl group", as used herein, means an alkyl group wherein all hydrogens on carbon atoms have been substituted by fluorines. In some embodiments of this invention, the perfluorinated alkyl group is a perfluorinated $C_1$-$C_6$ alkyl group. Examples of a perfluorinated $C_1$-$C_6$ alkyl group include —$CF_3$ and —$CF_2CF_3$.

The term "product selectivity to $CF_3CFClCH_3$", as used herein, means the molar percentage of $CF_3CFClCH_3$ obtained in the reaction of $CF_3CCl=CH_2$ with HF compared to the total molar amounts of all organic products obtained.

The term "product selectivity to $CF_3CF_2CH_3$", as used herein, means the molar percentage of $CF_3CF_2CH_3$ obtained in the reaction of $CF_3CCl=CH_2$ with HF compared to the total molar amounts of all organic products obtained.

The term "regioselectivity to $CF_3CFClCH_3$", as used herein, means the molar percentage of $CF_3CFClCH_3$ obtained in the reaction of $CF_3CCl=CH_2$ with HF compared to the total molar amounts of $CF_3CFClCH_3$ and $CF_3CHClCFH_2$ obtained.

The term "without substantially forming $R_fCF_2CH_3$" refers to the formation of $R_fCF_2CH_3$ in substantially small amounts, e.g., in less than about 2 mole % relative to the starting material $R_fCCl=CH_2$.

In addition, the term "without substantially forming $R_fCHClCH_2F$" refers to the formation of $R_fCHClCH_2F$ in substantially small amounts, e.g., in less than about 5 mole % relative to the starting material $R_fCCl=CH_2$.

Disclosed is a fluorination process comprising reacting a hydrohaloalkene of the formula $R_fCCl=CH_2$ with HF in a reaction zone in the presence of a fluorination catalyst selected from the group consisting of $TaF_5$ and $TiF_4$ in an amount effective and under conditions to produce a product mixture comprising a hydrohaloalkane of the formula $R_fCFClCH_3$, wherein $R_f$ is a perfluorinated alkyl group without substantially forming $R_fCF_2CH_3$ or $R_fCHClCH_2F$. This reaction is a liquid phase fluorination process.

In some embodiments of this invention, the desired product, i.e., hydrohaloalkane of the formula $R_fCFClCH_3$, is recovered from the product mixture.

In some embodiments of this invention, the hydrohaloalkene starting material is $CF_3CCl=CH_2$ (i.e., $R_f$ is $CF_3$), and the hydrohaloalkane product is $CF_3CFClCH_3$.

In some embodiments of this invention, the hydrohaloalkene starting material is $CF_3CF_2CCl=CH_2$ (i.e., $R_f$ is $CF_3CF_2$), and the hydrohaloalkane product is $CF_3CF_2CFClCH_3$.

In some embodiments of this invention, the fluorination catalyst is $TaF_5$. Typically, when the fluorination process is conducted in the presence of $TaF_5$, the temperature in the reaction zone is from about 90° C. to about 160° C. In some embodiments of this invention, the temperature is from about 95° C. to about 160° C. In some embodiments of this invention, the temperature is from about 95° C. to about 125° C. In still additional embodiments, the temperature of the reaction ranges from about 98° C. to about 114° C.

Typically, when the fluorination process is conducted in the presence of $TaF_5$, the amount of $TaF_5$ used for the reaction is at least 1 mole % of the amount of hydrohaloalkene of the formula $R_fCCl=CH_2$. In some embodiments of this invention, the amount of $TaF_5$ used for the reaction is at least 10 mole % of the amount of hydrohaloalkene of the formula $R_fCCl=CH_2$. In some embodiments of this invention, the amount of $TaF_5$ used for the reaction is at least 20 mole % of the amount of hydrohaloalkene of the formula $R_fCCl=CH_2$. In some embodiments of this invention, the amount of $TaF_5$ used for the reaction can be up to about 30 mole % based on the amount of hydrohaloalkene of the formula $R_fCCl=CH_2$. In some instances, the amount of $TaF_5$ used for the reaction is no more than 20 mole % of the amount of hydrohaloalkene of the formula $R_fCCl=CH_2$. Thus, in embodiments of the present invention, the amount of $TaF_5$ present in the reaction ranges from about 1 mole % to about 30 mol % of the hydrohaloalkene. In another embodiment, it ranges from about 10 mol % to about 20 mol % of hydrohaloalkene. Thus, in another aspect of the present invention the amount of $TaF_2$ used for the reaction is about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mole % of the amount of hydrohaloalkene.

In some embodiments of this invention, the fluorination catalyst is $TiF_4$. Typically, when the fluorination process is conducted in the presence of $TiF_4$, the temperature in the reaction zone is from about 90° C. to about 200° C. In some embodiments of this invention, the temperature is from about 120° C. to about 180° C. In some embodiments of this invention, the temperature is from about 140° C. to about 160° C.

Typically, when the fluorination process is conducted in the presence of $TiF_4$, the amount of $TiF_4$ used for the reaction is at least 1 mole % of the amount of hydrohaloalkene of the formula $R_fCCl=CH_2$. In some embodiments of this invention, the amount of $TiF_4$ used for the reaction is at least 10 mole % of the amount of hydrohaloalkene of the formula $R_fCCl=CH_2$. In some embodiments of this invention, the amount of $TiF_4$ used for the reaction is at least 35 mole % of the amount of hydrohaloalkene of the formula $R_fCCl=CH_2$. In some instances, the amount of $TiF_4$ used for the reaction is no more than 35 mole % of the amount of hydrohaloalkene of the formula $R_fCCl=CH_2$. Thus, in embodiments of the present invention, the amount of $TiF_4$ present in the reaction ranges from about 1 mol % to about 35 mol % of the hydrohaloalkene. In another embodiment, the amount of $TiF_4$ present ranges from about 10 mol % to about 30 mol % of the hydrohaloalkene. In another aspect of the present invention, the amount of $TiF_4$ present in the reaction is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 mole % of the amount of hydrohaloalkene.

$TaF_5$ and $TiF_4$ are commercially available. They can also be made through reactions of HF with $TaCl_5$ and $TiCl_4$ respectively at a temperature of from about 25° C. to about 180° C. In some embodiments of this invention, the temperature is from about 25° C. to about 130° C. In some embodiments of this invention, $TaF_5$ and $TiF_4$ are prepared just prior to being used in the fluorination processes. For example, in the same reactor used for the fluorination process, $TaCl_5$ or $TiCl_4$ can be treated with excess amount of HF. HCl generated from the reaction is released from the reactor, and the resulting $TaF_5$/HF or $TiF_4$/HF mixture can be used for the subsequent fluorination reaction.

Typically, the fluorination process of this disclosure is carried out in anhydrous or substantially anhydrous conditions, which means that water, which is detrimental to the reaction, should be excluded as much as possible from the reaction zone.

Typically, the fluorination process of this disclosure is carried out in a liquid phase. HF, hydrohaloalkene starting material, and hydrohaloalkane product can also function as solvents for $TaF_5$ and $TiF_4$ catalysts, and the fluorination process can be carried out without an additional solvent.

In some embodiments of this invention, the fluorination process is carried out in the presence of an additional solvent. Typically, the additional solvent is an inert chemical compound and shall not react with other chemical compounds or catalysts during the reaction. Such inert solvents, if used, should boil at a temperature enabling separation from the unconverted starting materials (HF and $R_fCCl=CH_2$) and from the desired product ($R_fCFClCH_3$). In some embodiments of this invention, the suitable inert solvent is a perfluorinated alkane. In some embodiments of this invention, the suitable inert solvent is a low molecular weight nitrile such as acetonitrile and propionitrile. In some embodiments of this invention, the additional solvent is a sulfone such as sulfolane.

The molar ratio of HF to hydrohaloalkene of the formula $R_fCCl=CH_2$ used in the fluorination reaction is typically from about 1:1 to about 100:1. In some embodiments of this invention, the molar ratio is from about 1:1 to about 20:1. In some embodiments of this invention, the molar ratio is from about 1:1 to about 10:1. In some embodiments of this invention, the molar ratio is from about 1:1 to about 5:1. In some embodiments of this invention, the molar ratio is from about 1:1 to about 2:1.

Typically, the fluorination process of this disclosure is conducted under autogenous pressure. In some embodiments of this invention, the pressure employed in the fluorination process is from about 100 psig to about 800 psig. In some embodiments of this invention, the pressure employed in the fluorination process is from about 100 psig to about 550 psig.

In some embodiments of this invention, the pressure employed in the fluorination process is from about 100 psig to about 270 psig.

The fluorination process of this disclosure can be carried out in batch reactors, continuous reactors or any combination of such reactors by methods known in the art. In some embodiments of this invention, HF and the fluorination catalyst are pre-mixed before contacting or reacting with hydrohaloalkene of the formula $R_fCCl=CH_2$. In some embodiments of this invention, hydrohaloalkene of the formula $R_fCCl=CH_2$ is fed to a reaction zone containing the mixture of HF and the fluorination catalyst. In some embodiments of this invention, hydrohaloalkene of the formula $R_fCCl=CH_2$ is co-fed with HF to a reaction zone containing the mixture of HF and the fluorination catalyst. In some embodiments of this invention, the mixture of HF and the fluorination catalyst is co-fed to a reaction zone with hydrohaloalkene of the formula $R_fCCl=CH_2$. In some embodiments of this invention, the fluorination catalyst is dissolved in an additional solvent before contacting with HF and hydrohaloalkene of the formula $R_fCCl=CH_2$.

In some embodiments, the present process is conducted in the presence of only one of the catalysts described hereinabove. In another aspect of the present process, the reaction is conducted in the presence of a mixture of the two catalysts described herein, as long as the total mole ratios of the catalysts are within the mole ratios of tantalum chloride, as described herein. In an embodiment, the present process is conducted in the absence of rate enhancing reagents, such as those described in U.S. Publication No. 2009/0018377, for example 1,1,2-trichloro-1-fluoroethane or trichloroethene. In other aspects of the present invention, such rate enhancing reagents may be present.

When $R_f$ is $CF_3$, it was found through experiments that the fluorination process of this disclosure provided high conversion of the $CF_3CCl=CH_2$ starting material. In some embodiments of this invention, the conversion of $CF_3CCl=CH_2$ during the fluorination process is at least 85%. In some embodiments of this invention, the conversion of $CF_3CCl=CH_2$ during the fluorination process is at least 90%.

When $R_f$ is $CF_3$, it was also found through experiments that the fluorination process of this disclosure produced the $CF_3CFClCH_3$ product with high selectivity. In some embodiments of this invention, the product selectivity to $CF_3CFClCH_3$ is at least 90 mole %. In some embodiments of this invention, the product selectivity to $CF_3CFClCH_3$ is at least 95 mole %. In some embodiments of this invention, the product selectivity to $CF_3CFClCH_3$ is at least 98 mole %. $CF_3CFClCH_3$ may be further fluorinated with HF to form $CF_3CF_2CH_3$.

The desired hydrohaloalkane product of the formula $R_1CFClCH_3$ can be recovered by well-known techniques. At the end of the fluorination reaction, the reaction may be quenched with water. The resulting highly acidic aqueous phase may be neutralized with a buffer solution, such as phosphates. The organic phase can be separated, dried and distilled to recover the desired hydrohaloalkane product. In some embodiments of this invention, the recovered hydrohaloalkane product of the formula $R_fCFClCH_3$ is at least 95 mole % pure. In some embodiments of this invention, the recovered hydrohaloalkane product of the formula $R_fCFClCH_3$ is at least 98 mole % pure.

The effluent from the fluorination reaction zone is typically a product mixture comprising unreacted starting materials ($R_fCCl=CH_2$ and HF), the catalyst, the desired hydrohaloalkane product of the formula $R_fCFClCH_3$, and some byproducts. The byproducts may include under-fluorinated compound $R_fCCl_2CH_3$ and over-fluorinated compound $R_fCF_2CH_3$. It was surprisingly found through experiments that the fluorination process, which is conducted as described herein, controls the generation of the $CF_3CF_2CH_3$ byproduct at a low level. When $R_f$ is $CF_3$, it was also found through experiments that the regioselectivity of the fluorination reaction of the process, as described herein, was very high. The fluorination reaction between $CF_3CCl=CH_2$ and HF may generate both isomers $CF_3CFClCH_3$ and $CF_3CHClCH_2F$. It was found that the fluorination process, which was conducted as described herein, generated substantially more $CF_3CFClCH_3$ than $CF_3CHClCH_2F$. In some embodiments of this invention, the regioselectivity to $CF_3CFClCH_3$ is at least 95 mole %. In some embodiments of this invention, the regioselectivity to $CF_3CFClCH_3$ is at least 98 mole %.

In some embodiments of this invention, the product selectivity to $CF_3CF_2CH_3$ is no more than 2 mole %. In some embodiments of this invention, the product selectivity to $CF_3CF_2CH_3$ is no more than 1 mole %. In other words, under the conditions described herein, the present process produces little, if any, products where the HF fluorinates the terminal carbon in $R_fCCl=CH_2$ and/or where the fluorine atom replaces the chlorine atom on the non-terminal carbon atom in $R_fCCl=CH_2$. The conditions described herein, e.g., the mole ratio of the catalyst to $R_fCCl=CH_2$ and the temperature of the reaction makes this reaction useful in the process of preparing tetrafluoropropenes, including 2,3,3,3-tetrafluoropropene (HFO-1234yf).

In an embodiment of the present invention, the fluorination process of the present invention is an intermediate process for preparing tetrafluoropropenes, including 2,3,3,3-tetrafluoropropene (HFO-1234yf).

Step 1A:

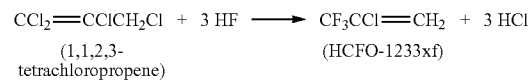
(1,1,2,3-tetrachloropropene)     (HCFO-1233xf)

Step 1B:

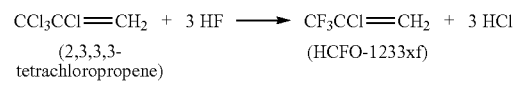
(2,3,3,3-tetrachloropropene)     (HCFO-1233xf)

Step 1C:

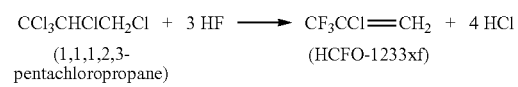
(1,1,1,2,3-pentachloropropane)     (HCFO-1233xf)

Step 2:

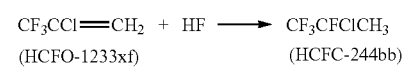
(HCFO-1233xf)     (HCFC-244bb)

Step 3:

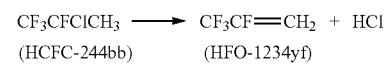
(HCFC-244bb)     (HFO-1234yf)

In the first step of the reaction, the chlorohydrocarbon is reacted with HF in the presence of a catalyst under fluorination conditions to produce $CF_3$ $CCl=CH_2$ (HCFC 1233xf). Three alternative reactions are provided, each with different starting materials. In one reaction, 1,1,2,3-tetrachloropropene is the starting material; in the second reaction, 2,3,3,3-tetrachloropropene is the starting material; while in the third reaction, 1,1,1,2,3-pentachloropropane is the starting material. In the third alternative the 1,1,1,2,3-pentachloropropane not only is fluorinated, but the reactant is also dehydrochlorinated to produce 2-chloro-3,3,3-trifluoropropene (HCFO- 1233xf). The second step of the reaction is the fluorination of HCFO-1233xf in the presence of a catalyst to produce 2-chloro-1,1,1,2-tetrafluoropropane (HCFC-244bb). The third reaction step is in the dehydrochlorination of HCFC 244bb to produce 2,3,3,3-tetrafluoropropene (HCFO-1234yf).

In the second step of the process, the 2-chloro-3,3,3-trifluoropropene (1233xf) is hydrofluorinated to form 3-chloro-1,1,1,2-tetrafluoropropane (244bb), which is then dehydrochlorinated to form the refrigerant 2,3,3,3-tetrafluoropropene (HFO-1234yl). One of the effects of the present process is to minimize the formation of 1,1,1,2,2-pentafluoropropane (245cb), for the formation of 245cb interferes with and makes it more difficult to conduct the dehydrochlorination reaction to form 2,3,3,3-tetrafluoropropene (HFO-1234yf). If too much catalyst is present, the reaction in the second step of the process completely fluorinates the HCFO-1233xf and forms 1,1,1,2,2-pentafluoropropane (245cb). If too much $R_fCCl=CH_2$ is present, then some of the $R_fCCl=CH_2$ is not fluorinated. However, by maintaining the reaction under the reaction conditions described hereinabove, the present process minimizes the formation of 1,1,1,2,2-pentafluoropropane (245cb) and $CF_3CHClCH_2F$ (1,1,1,3-terafluoro-2-chloropropane) and maximizes the formation of the desired product $CF_3CClFCH_3$.

Thus, another aspect of the present process is to prepare tetrafluoropropenes, including 2,3,3,3-tetrafluoropropene (HFO-1234yf)

According to one embodiment, the present invention includes a manufacturing process for making 2,3,3,3-tetrafluoroprop-1-ene using a starting material according to formula I:

$CX_2=CCl-CH_2X$ (Formula I)

$CX_3-CCl=CH_2$ (Formula II)

$CX_3-CHCl-CH_2X$ (Formula III)

wherein X is independently selected from F, Cl, Br, and I, provided that at least one X is not fluorine. In certain embodiments, the compound(s) of Formula I contains at least one chlorine, a majority of the Xs as chlorine, or all Xs as chlorine. In certain embodiments, the compound(s) of formula I include 1,1,2,3-tetrachloropropene (1230xa).

The method generally includes at least three reaction steps. In the first step, a starting composition of Formula I (such as 1,1,2,3-tetrachloropropene) is reacted with anhydrous HF in a first vapor phase reactor (fluorination reactor) to produce a mixture of 2-chloro-3,3,3-trifluoropropene (1233xf) and HCl. In certain embodiments, the reaction occurs in the vapor phase in the presence of a vapor phase catalyst, such as, but not limited to, a fluorinated chromium oxide. The catalyst may (or may not) have to be activated with anhydrous hydrogen fluoride HF (hydrogen fluoride gas) before use depending on the state of the catalyst.

While fluorinated chromium oxides are disclosed as the vapor phase catalyst, the present invention is not limited to this embodiment. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures and any one of which may be optionally fluorinated. In one embodiment, the catalyst is chrome oxide, such as for example, $Cr_2O_3$. Co-catalysts may also be present. Combinations of catalysts suitable for the first fluorination step nonexclusively include $Cr_2O_3$, $FeCl_3/C$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $COCl_2/AlF_3$, $NiCl_2/AlF_3$ and mixtures thereof. In one embodiment, the chrome oxide is present with a co-catalyst for fluorination reaction. Chromium oxide/aluminum oxide catalysts are described in U.S. Pat. No. 5,155,082, the contents of which are incorporated herein by reference. Chromium catalysts are also described in U.S. Pat. No. 3,258,500, the contents of which are also incorporated by reference. In another embodiment, Chromium (III) oxides such as crystalline chromium oxide or amorphous chromium oxide are used as catalysts, while in another aspect of the present invention, the catalyst for this fluorination step is amorphous chromium oxide. One such chromium oxide catalyst that is used in the first fluorination step is the activated chromium oxide gel catalyst, described in U.S. Pat. No. 3,258,500. Chromium oxide ($Cr_2O_3$) is a commercially available material which may be purchased in a variety of particle sizes.

The first fluorination reaction, according to the present invention, may be carried out under atmospheric pressure. In another embodiment, this reaction may be carried out under pressures of less than or greater than atmospheric pressures. For example, the process may be carried out, in one embodiment at a pressure ranging from about 0 psig to about 200 psig and in another embodiment, from about 0 psig to about 200 psig and in another embodiment from about 5 psia to about 100 psia.

The first fluorination reaction is conducted under condition effective for the conversion to 1233xf. In an embodiment, the temperature of the process may range from about 150° C. to about 400° C., in another embodiment from about 180° C. to about 400° C. In another embodiment, the temperature of the process ranges from about 180° C. to about 400° C., while in another embodiment, the temperature of the process is conducted from about 200° C. to about 300° C.

When the compound of formula I is 1,1,2,3,-tetrachloropropene (HFO-1230xa), the mole ratio of HF to 1230xa in step 1 of the reaction ranges from about 1:1 to about 50:1 and, in certain embodiments, from about 10:1 to about 20:1. The reaction between HF and HCFO-1230xa is carried out at a temperature from about 150° C. to about 400° C. (in certain embodiments, about 180° C. to about 300° C.) and at a pressure of about 0 psig to about 200 psig (in certain embodiments from about 5 psig to about 100 psig). Contact time of the 1230xa with the catalyst may range from about 1 second to about 60 seconds, however, longer or shorter times can be used.

The second step of the process is the hydrofluorination of 2-chloro-3,3,3-trifluoropropene (HCFO-1233xf), as described herein, to form 2-chloro-1,1,1,2-tetrafluoropropane (HCFC-244bb).

The third step of the present process is the dehydrochlorination of $R_fCFClCH_3$, such as, for example, 2-chloro-1,1,1,2-tetrafluoropropane (HCFC-244bb). The hydrohaloalkane product of the formula $R_fCFClCH_3$ may be dehydrochlorinated to produce a product mixture comprising a hydrofluoroalkene of the formula $R_fCF=CH_2$. Typically, the hydrohaloalkane of the formula $R_fCFClCH_3$ produced in the fluorination process above is first recovered from the product mixture and then dehydrochlorinated.

In some embodiments of this invention, the dehydrochlorination process is carried out by pyrolyzing $R_fCFClCH_3$ to produce $R_fCF=CH_2$. The term "pyrolyzing" or "pyrolysis", as used herein, means chemical change produced by heating in the absence of catalyst. The reactor for pyrolysis may be of any shape consistent with the process but is preferably a cylindrical tube, either straight or coiled. Heat is applied to the outside of the tube, the chemical reaction taking place on the inside of the tube. Of note are the reactors wherein the flow of gases through the reactor is partially obstructed to cause back-mixing, i.e. turbulence, and thereby promote mixing of gases and good heat transfer. This partial obstruction can be conveniently obtained by placing packing within the interior of the reactor, filling its cross-section or by using perforated baffles. The reactor packing can be particulate or fibrillar, preferably in cartridge disposition for ease of insertion and removal, has an open structure like that of Raschig Rings or other packings with a high free volume, to avoid the accumulation of coke and to minimize pressure drop, and permits the free flow of gas. In some embodiments of this invention, $R_f CFClCH_3$ is pyrolyzed at a temperature of from about 400° C. to about 700° C. to produce a product mixture comprising $R_f CF=CH_2$. Pyrolysis processes have also been disclosed in U.S. Patent Publication No. 2010-0105967, which is incorporated herein by reference.

In some embodiments of this invention, the dehydrochlorination process is carried out in the presence of a catalyst. Suitable catalysts for dehydrochlorination include carbon, metals (including elemental metals, metal oxides, metal halides, and/or other metal salts); alumina; fluorided alumina; aluminum fluoride; aluminum chlorofluoride; metals supported on alumina; metals supported on aluminum fluoride or chlorofluoride; magnesium fluoride supported on aluminum fluoride; metals supported on fluorided alumina; alumina supported on carbon; aluminum fluoride or chlorofluoride supported on carbon; fluorided alumina supported on carbon; metals supported on carbon; and mixtures of metals, aluminum fluoride or chlorofluoride, and graphite. Suitable metals for use on catalysts (optionally on alumina, aluminum fluoride, aluminum chlorofluoride, fluorided alumina, or carbon) include chromium, iron, and lanthanum. Typically, when used on a support, the total metal content of the catalyst will be from about 0.1 to 20 percent by weight; and in some embodiments from about 0.1 to 10 percent by weight. In some embodiments of this invention, catalysts for dehydrochlorination include carbon, alumina, and fluorided alumina. In some embodiments of this invention, carbon includes acid-washed carbon, activated carbon and three dimensional matrix carbonaceous materials. The catalytic dehydrochlorination processes have also been disclosed in U.S. Pat. No. 7,943,015, which is incorporated herein by reference.

In some embodiments of this invention, the dehydrochlorination process is carried out by reacting $R_f CFClCH_3$ with a basic aqueous solution to produce a product mixture comprising $R_f CF=CH_2$. As used herein, the basic aqueous solution is a liquid that is primarily an aqueous liquid having a pH of over 7; the liquid may be a solution, dispersion, emulsion, suspension or the like. In some embodiments of this invention, the basic aqueous solution has a pH of 8 or higher. In some embodiments of this invention, the basic aqueous solution has a pH of 10 or higher. In some embodiments of this invention, an inorganic base is used to form the basic aqueous solution. Such inorganic base can be selected from the group consisting of hydroxide, oxide, carbonate, and phosphate salts of alkali, alkaline earth metals and mixtures thereof. In some embodiments, such inorganic base is sodium hydroxide, potassium hydroxide, or mixtures thereof. In some embodiments of this invention, the basic aqueous solution is an aqueous solution of a quaternary ammonium hydroxide of the formula $NR_4OH$ wherein each R is independently hydrogen, a $C_1$ to $C_{16}$ alkyl group, aralkyl group, or substituted alkyl group, provided that not all R are hydrogens. Examples of $NR_4OH$ compounds useful in this invention are tetra-n-butylammonium hydroxide, tetra-n-propylammonium hydroxide, tetraethylammonium hydroxide, tetramethylammonium hydroxide, benzyltrimethylammonium hydroxide, hexadecyltrimethyammonium hydroxide, and choline hydroxide. Optionally, $R_f CFClCH_3$ is reacted with the basic aqueous solution in the presence of an organic solvent. In some embodiments of this invention, the organic solvent is selected from the group consisting of benzene and its derivatives, alcohols, alkyl and aryl halides, alkyl and aryl nitriles, alkyl, alkoxy and aryl ethers, ethers, amides, ketones, sulfoxides, phosphate esters and mixtures thereof. Optionally, $R_1 CFClCH_3$ is reacted with the basic aqueous solution in the presence of a phase transfer catalyst. As used herein, a phase transfer catalyst is intended to mean a substance that facilitates the transfer of ionic compounds into an organic phase from an aqueous phase or from a solid phase. The phase transfer catalyst facilitates the reaction between water-soluble and water-insoluble reaction components. In some embodiments of this invention, the phase transfer catalyst is selected from the group consisting of crown ethers, onium salts, cryptands, polyalkylene glycols, and mixtures and derivatives thereof. The phase transfer catalyst can be ionic or neutral.

The reactors, packings, distillation columns, and their associated feed lines, effluent lines, and associated units used in applying the processes of embodiments of this invention may be constructed of materials resistant to corrosion. Typical materials of construction include Teflon™ materials and glass. Typical materials of construction also include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

In the third step of 1234yf production, the 244bb is fed to a second vapor phase reactor (dehydrochlorination reactor) to be dehydrochlorinated to make the desired product 2,3,3,3-tetrafluoroprop-1-ene (1234yf). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, F, $Cl^-$, $Br^-$, and F. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monet 400, Inconel 825, Inconel 600, and Inconel 625.

Preferred, but non-limiting, catalysts include activated carbon, stainless steel (e.g. SS 316), austenitic nickel-based alloys (e.g. Inconel 625), nickel, fluorinated 10% CsCl/MgO, and 10% $CsCl/MgF_2$. The reaction temperature is preferably about 300-550° C. and the reaction pressure may be between about 0-150 psig. The reactor effluent may be fed to a caustic scrubber or to a distillation column to remove the by-product of HCl to produce an acid-free organic product which, optionally, may undergo further purification using one or any combination of purification techniques that are known in the art.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

LEGEND

| Abbreviation | Formula | Name |
|---|---|---|
| 1233xf | $CF_3CCl=CH_2$ | 2-chloro-3,3,3-trifluoropropene |
| 244bb | $CF_3CClFCH_3$ | 2-chloro-1,1,1,2-tetrafluoropropane |
| 245cb | $CF_3CF_2CH_3$ | 1,1,1,2,2-pentafluoropropane |
| 243ab | $CF_3CCl_2CH_3$ | 1,1,1-trifluoro-2,2-dichloropropane |
| 143a | $CF_3CH_3$ | 1,1,1-trifluoroethane |
| 243db | $CF_3CHClCH_2Cl$ | 1,1,1-trifluoro-2,3-dichloropropane |

Example 1

Example 1 demonstrates that the fluorination reaction of $CF_3CCl=CH_2$ in the presence of $TaF_5$ catalyst has a high $CF_3CCl=CH_2$ conversion and produces $CF_3CClFCH_3$ with high product selectivity and regioselectivity.

Preparation of $TaF_5$ Catalyst

Under anhydrous conditions, 30 grams (0.084 moles) of $TaCl_5$ was added to a 1 L Hastelloy™ reactor. The reactor was then evacuated and charged with 160 grams of anhydrous HF. The reactor was then heated at 120° C. while stirring for 1.5 hours under autogenous pressures. Then the reactor was cooled to less than 5° C., and HCl gas was removed by slowly venting the reactor into a caustic scrubber. At the end, a $TaF_5$/HF mixture was formed in the reactor.

Fluorination Reaction

The fluorination process in this example was run in a batch mode. The resulting $TaF_5$/HF mixture above was heated while stirring to 120° C. and 100 grams (0.766 moles) of 1233xf was added over a four-minute period. After the addition of all 1233xf the reactor was held at 120° C. for 5 hours under autogenous pressure. After 5 hours, the reactor was cooled to room temperature and 300 ml of water was added. The organics were evaporated from the reactor and collected in a cylinder chilled with dry ice. The cylinder contents were analyzed by GC/MS. Results show 93.3% conversion of 1233xf. The product distribution is listed in Table 1 below.

TABLE 1

| Components | GC area % |
|---|---|
| 244bb | 90.5 |
| 1233xf | 6.7 |
| 245cb | 1.7 |
| 243ab | 0.9 |

Example 2

Example 2 also demonstrates that the fluorination reaction of $CF_3CCl=CH_2$ in the presence of $TaF_5$ catalyst has a high $CF_3CCl=CH_2$ conversion and produces $CF_3CClFCH_3$ with high product selectivity and regioselectivity.

The procedure of Example 1 was followed except that 28 grams of $TaCl_5$ was used for the preparation of $TaF_5$. After the addition of all 1233xf, vapor samples were taken from the reactor at three-minute intervals and analyzed by GC/MS. The product distribution is listed in Table 2 below under "3 min", "6 min", "9 min", and "12 min" respectively.

After a total two-hour run time, the reactor was cooled to room temperature, and 300 grams of water was added to the reactor. The reactor was heated to 60° C. and the organics were vapor transferred into a collection cylinder chilled in dry ice. The cylinder contents were also analyzed by GC/MS. The result is shown in Table 2 below under "Product 120 min".

TABLE 2

| | time intervals | | | | |
|---|---|---|---|---|---|
| | 3 min | 6 min | 9 min | 12 min | Product 120 min |
| components | | GC area % | | | |
| 143a | 0.087 | 0.047 | 0.061 | 0.058 | 0.021 |
| 245cb | 0.978 | 0.907 | 1.631 | 1.776 | 6.57 |
| 244bb | 90.638 | 84.85 | 90.447 | 88.205 | 87.367 |
| 1233xf | 7.423 | 8.813 | 6.937 | 7.475 | 5.037 |
| 243ab | 0.148 | 1.055 | 0.242 | 0.66 | 0.824 |
| 243db | | | | | 0.046 |
| others | 0.558 | 3.927 | 0.232 | 1.798 | 0.126 |

Example 3

Example 3 demonstrates that the fluorination reaction of $CF_3CCl=CH_2$ in the presence of $TiF_4$ catalyst has a high $CF_3CCl=CH_2$ conversion and produces $CF_3CClFCH_3$ with high product selectivity and regioselectivity.

Preparation of $TiF_4$ Catalyst

Under anhydrous conditions, 36.23 grams (0.19 moles) of $TiCl_4$ was added to a 1 L Hastelloy™ reactor. The reactor was then evacuated and charged with 160 grams of anhydrous HF. The reactor was then heated at 120° C. while stirring for 1.5 hours under autogenous pressures. Then the reactor was cooled to less than 5° C. and HCl gas was removed by slowly venting the reactor into a caustic scrubber. At the end, a $TiF_4$/HF mixture was formed in the reactor.

Fluorination Reaction

The fluorination process in this example was run in a batch mode. The resulting $TiF_4$/HF mixture above was heated while stirring to 150° C. and 100 grams (0.766 moles) of 1233xf was added over a four-minute period. After the addition of all 1233xf the reactor was held at 150° C. under autogenous pressure, and vapor samples were taken from the reactor at sixty-minute intervals and analyzed by GC/MS. The product distribution is listed in Table 3 below under "60 min", "120 min", "180 min", and "240 min" respectively.

After a total five-hour run time, the reactor was cooled to room temperature, and 300 grams of water was added to the reactor. The reactor was heated to 60° C. and the organics were vapor transferred into a collection cylinder chilled in dry ice. The cylinder contents were also analyzed by GC/MS. The result is shown in Table 3 below under "Product 300 min".

TABLE 3

| components | time intervals | | | | product |
|---|---|---|---|---|---|
| | 60 min | 120 min | 180 min | 240 min | 300 min |
| | | | GC area % | | |
| 143a | 0.053 | 0.357 | 0.055 | 0.058 | 11.179 |
| 245cb | 0.233 | 0.745 | 0.120 | 0.261 | 6.150 |
| 244bb | 86.669 | 86.777 | 85.307 | 85.536 | 70.530 |
| 1233xf | 12.627 | 11.717 | 12.589 | 12.932 | 11.811 |
| 243ab | 0.306 | 0.403 | 1.251 | 1.149 | 1.112 |

Example 4

Preparation of TaF$_5$ Catalyst

A 1 gallon Hastelloy™ C autoclave equipped with a solid PTFE agitator was charged with TaCl$_5$ (500 gm) and HF (908 gm). The temperature of the reactor was raised to 100° C. for a period of 2 hours to convert TaCl$_5$ to TaF$_5$. The HCl generated was vented during the preparation process. The maximum pressure during the process was 140 psig. At the end, a TaF$_5$/HF mixture was formed in the reactor.

Fluorination Reaction

The fluorination process in this example was run in a continuous mode.

During the run, the resulting TaF$_5$/HF mixture above was maintained at a temperature of from 98° C. to 103° C. A starting material mixture comprising 99.2 mole % of 1233xf, 0.2 mole % of 244bb, and 0.6 mole % of unknowns was fed into the reactor at an average rate of 0.56 lb/hr, while HF was fed into the reactor at an average rate of 0.33 lb/hr. The reactor pressure was kept at 130 to 140 psig. Samples were taken from the effluent periodically and were analyzed by GC/MS. At the beginning, about 3.1 mole % 245cb was generated. After about 100 hours from the initiation of the process, the sample analysis indicated that less than 0.6 mole % of the 245cb was formed during the fluorination reaction. At about 200 hours from the initiation of the process, one sample analysis indicated that only 0.08 mole % of the 245cb was formed during the fluorination reaction. The reactor effluent sample analysis showed that the conversion of 1233xf was initially about 95 mole % and gradually decreased over the first 160 hours of the run down to 92 mole %. The rate of decrease of the 1233xf conversion accelerated after this time until the run was shut down after 243 hours because of lack of 1233xf feed material. The 1233xf conversion at the end of the 243 hours was about 77 mole %. The product selectivity to CF$_3$CFClCH$_3$ varied from 98.0 mole % to 99.9 mole % during the run. The product selectivity to CF$_3$CFClCH$_3$ near the end of the run is 99.9 mole %.

Example 5

Preparation of TaF$_5$ Catalyst

A 1 gallon Hastelloy™ C autoclave equipped with a solid PTFE agitator was charged with TaCl$_5$ (500 gm) and HF (928 gm). The temperature of the reactor was raised to 100° C. for a period of 2 hours to convert TaCl$_5$ to TaF$_5$. The HCl generated was vented during the preparation process. The maximum pressure during the process was 140 psig. At the end, a TaF$_5$/HF mixture was formed in the reactor.

Fluorination Reaction

The fluorination process in this example was run in a continuous mode.

During the 1$^{st}$ run, the resulting TaF$_5$/HF mixture above was maintained at a temperature of from 98° C. to 114° C. A starting material mixture comprising 18.2 mole % of 1233xf, 80 mole % of 244bb, and 1.6 mole % of 245cb was fed into the reactor at an average rate of 0.57 lb/hr, while HF was fed into the reactor at an average rate of 0.07 lb/hr. The reactor pressure was kept at 130 to 200 psig. Samples were taken from the effluent periodically and were analyzed by GC/MS. At the beginning, a lot of 245cb was generated. After about 50 hours from the initiation of the process, the sample analysis indicated that less than 0.5 mole % of the 245cb was formed during the fluorination reaction. At about 100 hours from the initiation of the process, one sample analysis indicated that only 0.05 mole % of the 245cb was formed during the fluorination reaction. The sample analysis showed that the effluent contained 3.0 mole % to 5.0 mole % of 1233xf and also showed that 244bb was the major product during the process. The 1$^{st}$ run lasted for 181 hours. The product selectivity to CF$_3$CFClCH$_3$ varied from 92.0 mole % to 99.9 mole % during the run. The product selectivity to CF$_3$CFClCH$_3$ near the end of the run is 99.9 mole %.

During the 2$^{nd}$ run, the 1233xf starting material with 99 mole % purity was fed into the reactor at a rate of 0.575 lb/hr, while HF was fed into the reactor at a rate of 0.375 lb/hr. The reactor temperature was maintained at 98° C. to 102° C., and the pressure was kept at 125 to 145 psig. During the course of the 2$^{nd}$ run, the 245cb formation dropped from 0.5 mole % to less than 100 ppm, and the unreacted 1233xf increased from 5 mole % to 20 mole %. The 2$^{nd}$ run lasted for 30 hours. The product selectivity to CF$_3$CFClCH$_3$ varied from 98.4 mole % to 99.9 mole % during the run. The product selectivity to CF$_3$CFClCH$_3$ at the initial period of the run is 98.4 mole %. The product selectivity to CF$_3$CFClCH$_3$ near the end of the run is 99.9 mole %.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A process comprising: reacting a hydrohaloalkene of the formula R$_f$CCl═CH$_2$ with HF in a reaction zone in the presence of a fluorination catalyst selected from the group consisting of TaF$_5$ and TiF$_4$ to produce a product mixture comprising a hydrohaloalkane of the formula R$_f$CFClCH$_3$, wherein $R_f$ is a perfluorinated alkyl group, in an amount effective to form $R_fCFClCH_3$ without substantially forming $R_fCF_2CH_3$ or $R_fCHClCH_2F$.

2. The process of claim 1, further comprising: recovering said hydrohaloalkane of the formula $R_fCFClCH_3$ from the product mixture.

3. The process of claim 1, wherein $R_f$ is $CF_3$.

4. The process of claim 3, wherein the product selectivity to $CF_3CFClCH_3$ is at least 90 mole %.

5. The process of claim 1, wherein said fluorination catalyst is $TaF_5$.

6. The process of claim 5, wherein the temperature in the reaction zone is from about 90° C. to about 160° C.

7. The process of claim 5 wherein the amount of $TaF_5$ present ranges from about 1 mole % to about 30 mole % of the amount of the hydrohaloalkene.

8. The process of claim 7 where the amount of $TaF_5$ present ranges from about 10 mol % to about 20 mol % of hydrohaloalkene.

9. The process of claim 1, wherein said fluorination catalyst is $TiF_4$.

10. The process of claim 9, wherein the temperature in the reaction zone is from about 90° C. to about 200° C.

11. The process of claim 9 wherein the amount of $TiF_4$ present ranges from about 1 mol % to about 30 mol % of the amount of hydrohaloalkene.

12. The process of claim 9 wherein the amount of $TiF_4$ ranges from about 10 mol % to about 30 mol % of hydrohaloalkene.

13. The process of claim 2, further comprising: dehydrochlorinating the recovered hydrohaloalkane of the formula $R_fCFClCH_3$ to produce a product mixture comprising a hydrofluoroalkene of the formula $R_fCF=CH_2$.

14. The process of claim 13, wherein $R_f$ is $CF_3$.

15. A liquid phase fluorination process for making $CF_3CFClCH_3$, comprising:
  feeding HF and an organic feed mixture comprising about 18.2 mole % of $CF_3CCl=CH_2$, about 80 mole % of $CF_3CFClCH_3$, and about 1.6 mole % of $CF_3CF_2CH_3$ to a reaction zone containing $TaF_5$ and HF; and
  reacting $CF_3CCl=CH_2$ from the organic feed mixture with HF in the reaction zone to produce additional $CF_3CFClCH_3$;
  wherein the temperature in the reaction zone is from about 98° C. to about 114° C., and the pressure in the reaction zone is from about 130 psig to about 200 psig.

16. A liquid phase fluorination process for making $CF_3CFClCH_3$, comprising:
  feeding HF and $CF_3CCl=CH_2$ to a reaction zone containing $TaF_5$ and HF; and
  reacting $CF_3CCl=CH_2$ with HF in the reaction zone to produce $CF_3CFClCH_3$;
  wherein the temperature in the reaction zone is from about 98° C. to about 103° C., and the pressure in the reaction zone is from about 125 psig to about 145 psig.

17. A process for preparing 2,3,3,3-tetrafluoroprop-1-ene comprising:
  a. providing a starting composition comprising at least one compound having a structure selected from Formulas I, II and III:

$CX_2=CCl—CH_2X$      Formula I $CX_3-CCl=CH_2$      Formula II $CX_3-CHCl=CH_2X$      Formula III wherein X is independently selected from F, Cl, Br and I, provided that at least one X is not fluorine:
  b. contacting said starting composition with a first fluorinating agent to produce a first intermediate composition comprising 2-chloro-3,3,3-trifluoropropene and a first chlorine-containing byproduct;
  c. contacting said first intermediate composition with a second fluorinating agent in the presence of a fluorination catalyst selected from the group consisting of $TaF_5$ and $TiF_4$ to produce a product comprising 2-chloro-1,1,1,2-tetrafluoropropane without substantially forming 1,1,1,2,2-pentafluoropropane or 1,1,1,3-terafluoro-2-chloropropane and
  d. dehydrochlorinating 2-chloro-1,1,1,2-tetrafluoropropane to produce a reaction product comprising 2,3,3,3-tetrafluoroprop-1-ene.

18. The process according to claim 17 wherein the product selectivity to $CF_3CF_2CH_3$ is no more than 2 mole %.

19. The process according to claim 17 wherein said fluorinaton catalyst $TaF_5$.

20. The process according to claim 19 wherein the amount of $TaF_5$ present ranges from about 1 mole % to about 30 mole % of the amount of 2-chloro-3,3,3-trifluoropropene and the temperature ranges from about 90° C. to about 160° C.

21. The process according to claim 17 wherein said fluorination catalyst is $TiF_4$.

22. The process according to claim 21 wherein the amount of $TiF_4$ present ranges from about 1 mol % to about 30 mol % of 2-chloro-3,3,3-trifluoropropene and the temperature ranges from about 90° C. to about 200° C.

* * * * *